United States Patent [19]

Yamashita et al.

[11] Patent Number: 5,439,811
[45] Date of Patent: Aug. 8, 1995

[54] METHOD FOR PREPARING AMINOACYL- AND MISAMINOACYL-TRNA

[75] Inventors: Nobuhiko Yamashita, Takatsuki; Junichi Tohyama, Ohtsu; Chiwa Kataoka, Kyoto; Kazunobu Miura, Nagaokakyo, all of Japan

[73] Assignee: Osaka Gas Company Limited, Osaka, Japan

[21] Appl. No.: 212,708

[22] Filed: Mar. 14, 1994

[30] Foreign Application Priority Data

Mar. 18, 1993 [JP] Japan .................................. 5-058549

[51] Int. Cl.⁶ .................. C12P 19/34; C07H 21/02
[52] U.S. Cl. ...................... 435/91.53; 435/91.3; 435/91.5; 536/124
[58] Field of Search .................. 435/91.3, 91.5, 91.53; 536/124

[56] References Cited

U.S. PATENT DOCUMENTS 4,568,640 2/1986 Rubin ..................................... 435/70

OTHER PUBLICATIONS

Lewin, Benjamin M., Genes, 2d. Ed., pp. 158–59 (1985).
Heckler, T. G., et al., Biochemistry 23, 1468–1473 (1984).
Noren, C. J., et al., Science 244, 182–188 (1989).
Gallego, M. E., et al., Biochimica et Biophysica Acta 696, 57–65 (1982).
Fereiro, C., et al., Biochimica et Biophysica Acta 882, 410–418 (1986).
Takai, H., et al., "Enzymatic Synthesis of Caerulein Peptide" in Peptide Chemistry 1980, Okawa, K., editor, pp. 213–218, Protein Research Foundation, 1981.
Jost, J. P., et al., J. Biol. Chem. 244, 5866–5873 (1969).
DeGroot, N., et al., Biochimica Biophysica Acta 186, 286–296 (1969).
Nishimura, S., "Biochemistry Experimental Course", Japan, Biochemical Society Ed (Tokyo Kagaku Dojin), vol. 7, pp. 429–435, 1975.
Louie, A., et al., Anal. Biochem. 141, 402–408 (1984).

Primary Examiner—David M. Naff
Assistant Examiner—Francisco C. Prats

[57] ABSTRACT

A method for preparing aminoacyl- and misaminoacyl-tRNAs utilizing a specific aminoacyl-tRNA hydrolase is provided. According to the present method, aminoacyl-tRNAs consisting of a tRNA and a corresponding amino acid, or misaminoacyl-tRNAs consisting of a tRNA and a non-corresponding amino acid or an amino acid derivative, can be prepared. In a specific embodiment, L-tyrosyl-tRNA$^{Tyr}$ is prepared using aminoacyl-tRNA hydrolase from *Fusarium culmorum* or *Artemia salina*. In another embodiment a misacylated tRNA, L-phenylalanyl-tRNA$^{Tyr}$, is prepared using the aminoacyl-tRNA hydrolase.

2 Claims, 3 Drawing Sheets

METHOD FOR PREPARING AMINOACYL- AND MISAMINOACYL-TRNA

FIELD OF THE INVENTION

The present invention relates to a method for preparing aminoacyl-tRNAs and misaminoacyl-tRNAs utilizing a specific aminoacyl-tRNA hydrolase.

PRIOR ART

At present, a method for preparing proteins utilizing a genetic engineering technique or protein engineering technique is one of the most important methods in biotechnology. The method enables one to produce a large amount of proteins with considerable readiness, but has disadvantages that i) it is difficult to purify a desired protein from a host cell, ii) some proteins prepared by the method are insoluble or unstable, and iii) proteins prepared by the method may be contaminated by a toxin in certain host cells. Moreover, amino acids used in host cells are limited to the 20 L-amino acids which constitute naturally occurring proteins, and other amino acids such as artificial amino acids cannot be used, with a few exceptions. This is because an amino acid must be first activated to become an aminoacyl-tRNA by an aminoacyl-tRNA synthase before being used as a substrate in systems for in vivo protein synthesis, and the amino acid recognized by the aminoacyl-tRNA synthase is limited to any one of the 20 L-amino acids.

On the other hand, systems for in vitro protein synthesis are those in which various components used in in vivo protein synthesis (i.e., a protein synthesis with a recombinant DNA technique) are taken into a test tube and the protein synthesis is performed steadily and effectively in vitro by reacting the components in the test tube. The components are ribosome, mRNA, L-amino acids, tRNAs corresponding to these amino acids, aminoacyl-tRNA synthases (ARS), other factors for protein synthesis, and the like.

In the above systems, if a misaminoacyl-tRNA is added instead of an aminoacyl-tRNA, it is possible to synthesize a variant protein in which a certain amino acid is replaced with other amino acid, or an artificial protein having a non-naturally occurring amino acid introduced. Such variant or artificial proteins or peptides are useful as such and also as functional materials. The functional materials can be used to develop novel substances having a variety of functions useful in energy, light, surface and separation technologies, or biotechnology. In particular, the functional materials are expected to be applied in the near future in techniques for a) immobilization of carbon dioxide, b) bioreactors, c) biosensors, or the like. Therefore, a technique for synthesizing misaminoacyl-tRNA is very important in the systems for in vitro protein synthesis.

A method for synthesizing misaminoacyl-tRNAs has been disclosed by Hecht et al. (reference 1; all the references cited herein are listed below). The method comprises the steps of chemically synthesizing dinucleotide pCpA and chemically binding an amino acid to the 3'-terminus of pCpA by an ester bond to obtain aminoacyl-pCpA. On the other hand, tRNA is partially digested with venom phosphodiesterase to obtain tRNA-C-OH lacking pCpA at its 3'-terminus. Subsequently, the aminoacyl-pCpA is enzymatically linked to the 3'-terminus of tRNA-C-OH using RNA ligase to obtain aminoacyl-tRNA. Shultz et al. (reference 2) used this method and prepared misaminoacyl-tRNAs by binding a variety of non-naturally occurring amino acids to a modified tRNA which was prepared by converting anticodon of E. coli tRNA$^{Phe}$ (tRNA specific to phenylalanine; such tRNA is referred to as "tRNA$^{Phe}$" hereinafter, and so on) into CUA so that the amber codon (UAG) can be translated. However, such a chemical method for synthesizing misaminoacyl-tRNAs has disadvantages in that the steps of synthesizing aminoacyl-pCpA are complicated because addition and elimination of protecting groups and purification must be repeated, and the yield of the resulting misaminoacyl-tRNAs is low because of the cleavage of the unstable aminoacyl linkage.

On the contrary, it is believed that a method for enzymatically synthesizing aminoacyl-tRNA is excellent in efficiency, stability, and yield. In cells, the binding of an amino acid and tRNA is catalyzed by aminoacyl-tRNA synthetase (ARS). This enzyme is the only one known to be used in synthesizing aminoacyl-tRNA in vivo and has a very high specificity to its substrate. It is said that correspondence between one of the 20 L-amino acids (e.g., phenylalanine) and tRNA corresponding to the amino acid (tRNA$^{Phe}$) is strictly ruled, and the frequency of erroneous recognition is one per several ten-thousands.

It is known that the enzyme synthesizes aminoacyl-tRNA by a two-step reaction. First, ARS specific to an amino acid consumes ATP and aminoacyl adenylic acid is synthesized. This aminoacyl adenylic acid, which is an intermediate, remains binding to the amino acid-specific ARS. Then, OH group of adenosine in pCpCpA which represents 3'-terminus of amino acid-specific tRNA, and COOH group of the activated amino acid (the above intermediate) are linked through an ester bond to give aminoacyl-tRNA.

From the 1980s, amino acid-activating mechanism and catalytic function of ARS, as well as the relationship between the structure and activity of ARS have been studied. However, up to now, there is no report as to alterations in substrate specificity by modifying ARS, such as alterations in specificity by modifying the active center of ARS. Also, the ability of tRNA to accept an amino acid has been studied. As a site in tRNA required for recognition by ARS, the anticodon site, acceptor stem site, and several bases and base pairs located on each loop in a loop-like structure in tRNA are pointed out, and it is believed that in order to alter the ability of tRNA to accept an amino acid, modification of such sites may be required. One example of alteration of this ability of tRNA by modifying the anticodon site alone has been reported. However, the results indicated that acceptable amino acids were limited and that the ability of modified tRNA to accept amino acids was lower than that of unmodified tRNA. Thus, it is now difficult to alter ARS and tRNA so that they can recognize and accept the desired amino acids. Therefore, it is difficult at present to prepare mischarged aminoacyl-tRNAs (e.g., glycine-tRNA$^{Phe}$) by the use of ARS.

BRIEF DESCRIPTION OF THE INVENTION

The present invention provides a novel method for enzymatically preparing aminoacyl-tRNAs or misaminoacyl-tRNAs to be used in systems for in vitro protein synthesis. In more detail, the present invention provides a method for preparing an aminoacyl-tRNA or misaminoacyl-tRNA comprising binding tRNA and a corresponding amino acid, non-corresponding amino acid, or amino acid derivative utilizing the reverse reaction of a specific aminoacyl-tRNA hydrolase as shown below:

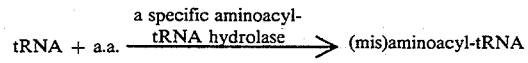

$$\text{tRNA} + \text{a.a.} \xrightarrow{\text{a specific aminoacyl-tRNA hydrolase}} \text{(mis)aminoacyl-tRNA}$$

wherein a.a. represents an amino acid or amino acid derivative, and a specific aminoacyl-tRNA hydrolase represents an aminoacyl-tRNA hydrolase with a broad substrate specificity.

DETAILED DESCRIPTION OF THE INVENTION

Figure 1:
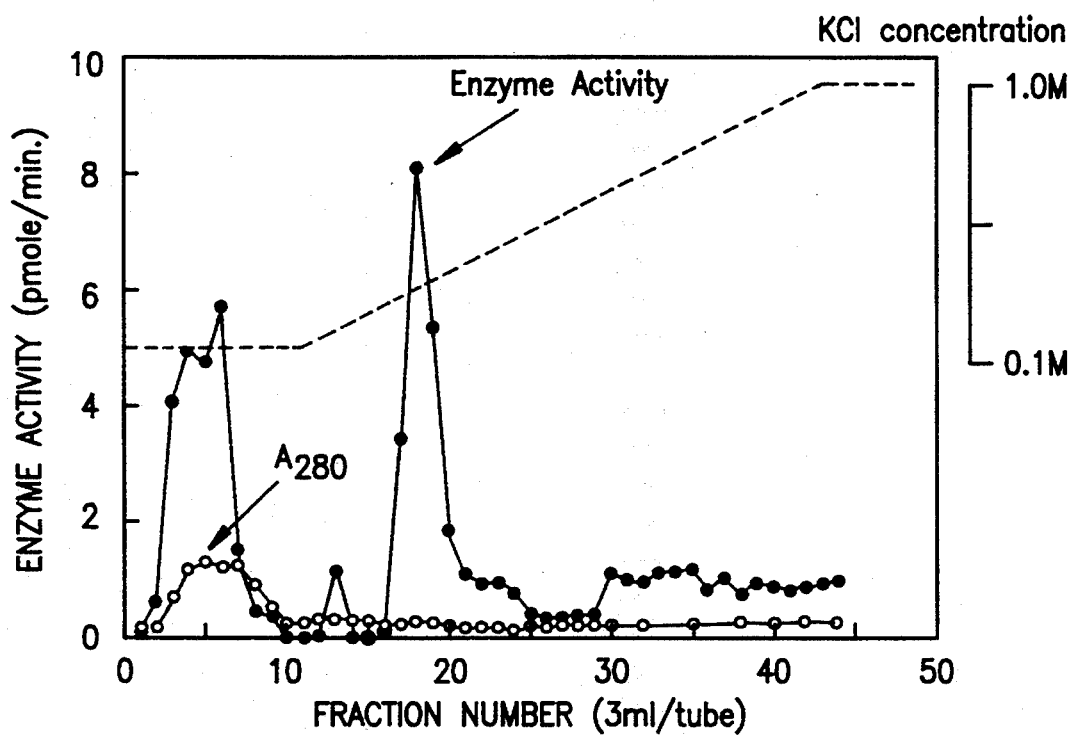
FIG. 1 is a graph depicting the result of fractionation of the aminoacyl-tRNA hydrolase derived from *Fusarium culmorum* by an ion exchange chromatography.

In the method of the present invention, a specific aminoacyl-tRNA hydrolase is used. That is, an enzyme with a broad substrate specificity is selected from aminoacyl-tRNA hydrolases and the reverse reaction of such enzyme is used.

Heredia et al. found hydrolases from *Artemia larvae* (reference 3) and *Fusarium culmorum* (reference 4) that specifically hydrolyze aminoacyl-tRNAs to generate an amino acid and tRNA. It has been reported that these hydrolases, aminoacyl-tRNA hydrolases (ARH), have a broad substrate specificity and show equal activities to hydrolyze several aminoacyl-tRNAs, such as phenylalanine-tRNA, lysine-tRNA, and leucine-tRNA.

It is also known that the reverse reactions of hydrolases efficiently proceed under certain conditions. For example, a variety of peptides are synthesized by the reverse reaction of protein hydrolases, such as papain, α-chymotrypsin, carboxypeptidase Y, trypsin, and pepsin (reference 5).

The inventors suspected that it is possible to aminoacylate tRNA with a desired amino acid by utilizing the reverse reaction of a specific ARH and carried out an intensive research. As a result, the present invention has been completed.

Specific ARHs used in the method of the present invention are those with a broad substrate specificity. For example, ARHs derived from the above-mentioned *Artemia larvae* and *Fusarium culmorum* can be used. *Artemia larvae* can be obtained by culturing *Artemia salina* durable eggs, which are commercially available as feed for fish. The eggs can be obtained from Nisshin Fine Chemical Inc. (Yokohama), USC International Company (Tokyo), or the like. The *Fusarium culmorum* strain can be obtained from Institute for Fermentation, Osaka (IFO) or American Type Culture Collection (ATCC).

Aminoacyl-tRNA hydrolases (EC 3.1.1.29) are also found in *E. coli*, yeast, and animal tissues in addition to the above-mentioned sources. These enzymes are reported to specifically hydrolyze aminoacyl-tRNAs in which the N terminus of an amino acid is modified, and not to hydrolyze unmodified aminoacyl-tRNAs (references 6 and 7). For the incorporation of a variety of amino acids into tRNA by the reverse reaction of ARH, it is preferable to select ARH having a broad substrate specificity to aminoacyl-tRNAs. At present, other ARH than those derived from the above mentioned sources is not known. However, ARHs suitable for the present invention and derived from other sources may be discovered in future, because research on distribution and physiological functions of ARH has not proceeded yet. Such ARHs with a broad substrate specificity that may be discovered in the future also can be used in the present invention.

ARHs can be isolated and purified from cells by the methods known in the art.

Starting materials in conducting the method of the present invention, such as tRNA, naturally occurring amino acids, and non-naturally occurring amino acids are commercially available or can be synthesized by the method described in the literature.

Reaction systems utilizing the reverse reaction of ARH can be constructed by making reference to reverse reactions of hydrolases, such as protease, sugar hydrolase, lipase, phosphatase, and the like.

For example, in a method for enzymatically synthesizing peptides utilizing the reverse reaction of the hydrolysis reaction of a protease, several modified condensation reaction systems have been developed to obtain products effectively. Theoretically, the equilibrium reaction proceeds reversely if the reaction products are removed from the reaction system. For example, the N-terminal amino group of a carboxyl component and the C-terminal carboxyl group of an amine component that are not involved in the reaction may be protected with protecting groups to prevent side reactions and to decrease the solubility of the resulting peptides, whereby precipitating and removing said peptides from the reaction system. Peptides can be also synthesized in a micelle in a biphase system consisting of water and a water-immiscible organic solvent wherein hydrophobic products are taken into the organic phase and removed from the reaction system.

The conditions for accelerating the reverse reaction are described below: (1) concentration of materials: increase of concentration of one of materials in an enzymatic reaction system accelerates the reverse reaction according to the law of mass action; (2) concentration of enzyme: the molar ratio of the enzyme to the materials for accelerating the reverse reaction is generally 1:several hundreds to several thousands; (3) reaction time, temperature and pH: optimal time, temperature, and pH for the reverse reaction are examined and established.

An aminoacyl-tRNA resulting from the reverse reaction by ARH and an unreacted tRNA can be separated from each other by a variety of chromatographic techniques. For example, tRNAs bound to hydrophobic amino acids, such as tyrosine and phenylalanine, can be separated from unreacted tRNAs on a benzoylated Sepharose column because the bound tRNAs are highly hydrophobic relative to the unreacted tRNAs (reference 8). Moreover, elongation factor for protein synthesis (EF-Tu) forms a complex together with GTP and functions to specifically bind an aminoacyl-tRNA. Such property enables one to separate an aminoacyl-tRNA from an unreacted tRNA utilizing a column immobilized with said factor (reference 9).

The present invention is further illustrated by the following Examples, but should not be construed to be limited thereto.

EXAMPLE 1

Preparation of ARH from *Fusarium culmorum* and measurement of its activity

A. Culture of *Fusarium culmorum*

*Fusarium culmorum* strain (IFO No. 6814) was obtained from Institute for Fermentation, Osaka (IFO), inoculated on a slant culture medium (potato-agar medium: 200 g of potato, 20 g of cane sugar, and 15 g of agar were mixed, the pH of the mixture was adjusted to pH 5.6, and distilled water was added to the mixture to make a final volume of 1000 ml), and cultured at 60% humidity and at temperature of 24° C. for 10 to 14 days. Then, the cultured cells (1 ese) were inoculated in a liquid medium (including 0.5 g of $KH_2PO_4$, 0.02 mg of $MnCl_2 \cdot 4H_2O$, 0.5 g of $MgSO_4 \cdot 7H_2O$, 0.02 mg of $NaMoO_4 \cdot 2H_2O$, 0.5 mg of $FeSO_4 \cdot 4H_2O$, 1 mg of thiamin hydrochloride, 0.5 mg of $ZnSO_4 \cdot 7H_2O$, 20 g of D-glucose, 0.02 mg of $CuSO_4 \cdot 5H_2O$, 2 g of L-asparagine, and 2 g of casamino acid in 1 L) and cultured with shaking at 24° C. for 67 hours. The culture was then filtered though No. 2 filter, and the cells were recovered and washed with sterilized water for three times. The recovered cells were weighed and stored at −20° C.

B. Partial purification of ARH

The ARH derived from *Fusarium culmorum* was partially purified by the method of Heredia et al. (reference 4). That is, to the cells stored at −20° C. was added five volumes of buffer A (50 mM Tris-HCl buffer (pH 7.0) including 10 mM magnesium acetate and 10 mM mercaptoethanol). Then the cells were thawed on ice with shaking, and homogenized for 5 strokes by a teflon homogenizer. The homogenate was centrifuged at 10,000×g for 10 min at 4° C. and the supernatant was further centrifuged at 105,000×g for 90 min at 4° C. The resulting supernatant was incubated at 30° C. for 16 hours to obtain a crude extract of ARH. The crude ARH was fractionated by an ion exchange chromatography on a CM-Sephadex C25 column. The column (16×100 mm) was previously equilibrated using buffer B (buffer A containing 0.1M KCl). The crude ARH (25 ml, 8.6 mg protein/ml) was applied to the column at a rate of 0.5 ml/minute. The column was washed with buffer B and then eluted with a linear gradient of 0.1M to 1 M KCl in buffer B (100 ml). Three ml fractions were collected and 50 μl of each fraction was used to determine the ARH activity. As a substrate, [$^{14}$C]-phenylalanyl-tRNA was used. The concentration of the protein was determined by measuring absorbance at 280 nm. Fractions with the ARH activity were pooled to obtain a partially purified ARH solution.

C. Measurement of ARH activity

The ARH activity was determined by hydrolyzing a labeled aminoacyl-tRNA and measuring the amount of remaining labeled aminoacyl-tRNA according to the method of Heredia et al. (reference 4).

C-1. Preparation of labeled aminoacyl-tRNA $tRNA^{Phe}$, $tRNA^{fMet}$, $tRNA^{Tyr}$, and aminoacyl-tRNA synthetase (derived from *E. coli*) were purchased from SIGMA CHEMICAL COMPANY. $tRNA^{Glu}$ was purchased from Boehringer Mannheim.

[$^{14}$C]-phenylalanyl-tRNA, [$^{14}$C]-formylmethionyl-tRNA, [$^{14}$C]-tyrosyl-tRNA, and [$^{14}$C]-glutamic acidyl-tRNA were prepared according to the method of Nishimura et al. (reference 10). Thus, 60 μl of 1 M Tris-HCl (pH 7.7), 30 μl of 80 mM adenosine triphosphate (ATP) solution (pH 7.0), 30 μl of 0.8 M KCl, 30 μl of 0.2 M $MgCl_2$, 40 μl of amino acid-specific tRNA solution (200 DU/ml: 1.3 to 1.4 mg/ml), 80 μl of each [$^{14}$C]-amino acid (50 μCi/ml), and 10 μl of aminoacyl-tRNA synthetase (35 U/μl) were mixed and water was then added to make 300 μl of final volume. In order to prepare [$^{14}$C]-glutamic acidyl-tRNA, 0.1M Tris-HCl (pH 7.7) was used instead of 1 M Tris-HCl (pH 7.7).

The aminoacylation reactions were done by incubating the reaction mixtures for 30 minutes at 37° C. After the reactions, one twentieth (15 μl) of the reaction mixture was taken and added to 3 ml of ice-cold 5% TCA to precipitate the aminoacyl-tRNA. The mixture was allowed to stand on ice for 15 minutes and filtered with aspiration through a GF/C glass filter (Whatman International Ltd.) to recover precipitate. The filter was washed three times with 5% TCA and once with 50% ethanol/50% ethyl ether and dried. The filter was then put in a toluene scintillator (5 ml) and the radioactivity of the filter was measured by a scintillation counter to determine the amount of the labeled amino acid bound to tRNA. To the remaining reaction mixture was added equal volume (300 μl) of a saturated phenol solution in 10 mM Tris-HCl buffer (pH 7.0) containing 1 mM EDTA and the resulting mixture was stirred and centrifuged at 10,000 Xg for 2 minutes. To the aqueous layer (the upper layer), 60 μl of 5 M NaCl was added to make final concentration of 1 M, and two volumes (720 μl) of −20° C. ethanol was then added. The resulting mixture was allowed to stand at −20° C. for 30 minutes and then centrifuged at 10,000 Xg at 4° C. for 10 minutes to precipitate a tRNA fraction. The precipitated fraction was dried in vacuum and dissolved in sterilized water to make a labeled aminoacyl-tRNA solution.

C-2. Measurement of ARH activity

10 μl of 500 mM imidazole hydrochloride (pH 7.5), 10 μl of 10 mM magnesium acetate, 10 μl of 3000 to 5000 cpm/μl [$^{14}$C]-labeled aminoacyl-tRNA, and 20 to 50 μl of sample for measurement were mixed and water was then added to make 100 μl of total volume. The mixture was allowed to stand at 30° C. for 30 minutes. To the mixture, 3 ml of ice-cold 5% TCA was added. The resulting mixture was allowed to stand on ice for 15 minutes and then filtered with aspiration through a GF/C glass filter to recover precipitate. The filter was washed three times with 5% TCA and once with 50% ethanol/50% ethyl ether and then dried. The filter was then put in a toluene scintillator (5 ml) and the radioactivity of the remaining labeled aminoacyl-tRNA in the precipitate was measured by a scintillation counter to determine the amount of a decomposed aminoacyl-tRNA. The enzyme activity decomposing 1 μM aminoacyl-tRNA per minute was defined as 1 U.

D. Results 7.4 g of cells were obtained from 50 ml culture of *Fusarium culmorum*. ARH was partially purified from the cells by an ion exchange chromatography on a CM-Sephadex C-25 column according to the report of Heredia et al. As a result, about 10 μg protein of crude ARH was obtained. ARH was eluted with 0.35M to 0.4M KCl from the ion exchange chromatography (FIG. 1). This result is consistent with that described in Heredia et al.

To examine the crude ARH for specificity to a substrate, 4 types of labeled aminoacyl-tRNAs were used as the substrate to determine the specificity of the crude ARH. The results indicated that the activity to decompose 4 types of labeled aminoacyl-tRNAs was almost equal and the enzyme had a broad substrate specificity (Table 1).

TABLE 1

Hydrolase activity of crude aminoacyl-tRNA hydrolase derived from *Fusarium culmorum* to decompose a variety of aminoacyl-tRNAs

| Aminoacyl-tRNA | Activity of enzyme (pmol/min/μg protein) |
| --- | --- |
| [$^{14}$C] Phe-tRNA$^{Phe}$ | 1.5 |
| [$^{14}$C] Met-tRNA$^{fMet}$ | 1.0 |
| [$^{14}$C] Glu-tRNA$^{Glu}$ | 2.3 |
| [$^{14}$C] Tyr-tRNA$^{Tyr}$ | 1.5 |

In addition, the crude ARH had no ribonuclease activity. These results indicated that the enzyme prepared herein from *Fusarium culmorum* is identical to that described in Heredia et al.

EXAMPLE 2

Synthesis of aminoacyl-tRNA from L-tyrosine and tyrosine-specific tRNA utilizing reverse reaction of ARH derived from *Fusarium culmorum*

A. Method

Aminoacylation of tRNA utilizing an aminoacyl-tRNA hydrolase was carried out by subjecting an amino acid and tRNA to a condensation reaction in the presence of an organic solvent. Thus, 10 μl of 0.5 M HEPES buffer, 10 μl of 100 mM magnesium acetate, 25 μl of dimethyl formamide, 10 μl of 20 U/ml tRNA$^{Tyr}$, 10 μl of 40 mM L-tyrosine, 10 μl of 1 mCi/ml L-[2,3,4,5,6-$^3$H] tyrosine, and 2.5 μU of partially purified ARH were mixed and water was then added to make 110 μl of final volume. The reaction mixture was incubated at 30° C. for 15 minutes. As a control, a similar reaction was carried out in the absence of ARH. After the reactions, aminoacyl-tRNAs and free amino acids in the reaction mixtures were separated by high performance molecular sieve chromatography on Shodex PROTEIN KW-803 columns (8 mm×30 cm, paired). The columns were previously equilibrated using 10 mM Tris-Cl buffer (pH 7.5) containing 60 mM NH$_4$Cl and 10 mM (CH$_3$COO)$_2$Mg. The reaction mixture (50 μl) was applied to the column and developed at a rate of 1.0 ml/min. Fractions were collected in 0.5 ml portions. To 0.5 ml of each fraction was added 3 ml of liquid scintillation cocktail Ready Safe (BECKMAN Instrument, Inc.) and the radioactivity of the mixture was measured by a liquid scintillation counter (BECKMAN Model LS5000TD). Protein markers for molecular weight determination on HPLC were purchased from Oriental Yeast Co., Ltd. The markers used were glutamic dehydrogenase (Mw 290,000), lactate dehydrogenase (Mw 142,000), enolase (Mw 67,000), adenylate kinase (Mw 32,000), and cytochrome C (Mw 12,400).

B. Results

Figure 2:
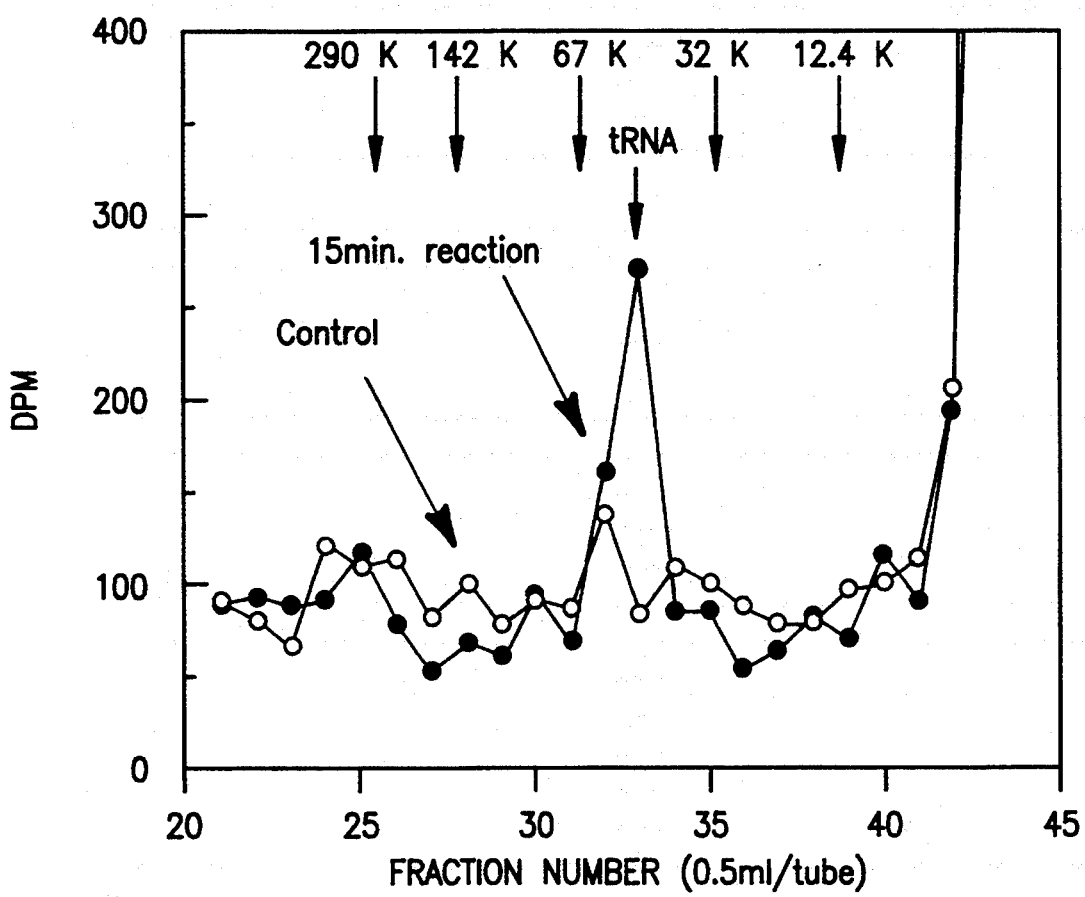
FIG. 2 is a graph depicting the result of fractionation of tyrosyl-tRNA$^{Tyr}$ formed by the reverse reaction of aminoacyl-tRNA hydrolase by HPLC analysis.

To examine whether an aminoacyl-tRNA can be synthesized by the reverse reaction of ARH, the hydrolytic activity of ARH was suppressed by adding an organic solvent and a large excess of an amine component (L-tyrosine) to a reaction system, and a condensation reaction of the amino acid and tRNA was accelerated. L-tyrosine and tyrosine-specific tRNA were reacted using the enzyme in the presence of 23% dimethyl formamide, and the amount of the labeled amino acid incorporated into a tRNA fraction was measured by high performance molecular sieve chromatography. As a result, it was found that no labeled amino acid was incorporated into the tRNA fraction in the absence of ARH, while a significant increase of a radioactive peak was observed at the same position as that of Tyr-tRNA$^{Tyr}$ in the presence of ARH (FIG. 2).

The tRNA fraction which showed incorporation of tyrosine was phenol extracted and ethanol precipitated to recover the tRNA. Most of the radioactivity was detected in the tRNA. The fraction containing the tRNA was then treated with ARH, again phenol extracted, and ethanol precipitated. In this case, the labeled amino acid was detected in the supernatant after the ethanol precipitation. These results indicate that in the presence of 23% dimethyl formamide and a large excess of L-tyrosine, the hydrolytic activity of ARH was suppressed and tyrosyl-tRNA was synthesized from L-tyrosine and tyrosine-specific tRNA by the reverse reaction (condensation) of ARH.

EXAMPLE 3

Synthesis of misaminoacyl-tRNA from L-phenylalanine and tyrosine-specific tRNA utilizing reverse reaction of ARH derived from *Fusarium culmorum*

A. Method

Aminoacylation of tRNA utilizing an aminoacyl-tRNA hydrolase was carried out by subjecting an amino acid and tRNA to a condensation reaction in the presence of an organic solvent. Thus, 10 μl of 0.5 M HEPES buffer, 10 μl of 100 mM magnesium acetate, 25 μl of dimethyl formamide, 10 μl of 20 U/ml tRNA$^{Tyr}$, 10 μl of 40 mM L-phenylalanine, 10 μl of 1 mCi/ml L-[2,3,4,5,6-$^3$H] phenylalanine, and 2.5 μU of partially purified ARH were mixed and water was then added to make 115 μl of final volume. The reaction mixture was incubated at 30° C. for 15 minutes. As a control, a similar reaction was carried out in the absence of ARH. After the reactions, aminoacyl-tRNAs and free amino acids in the reaction mixtures were separated by high performance molecular sieve chromatography on Shodex PROTEIN KW-803 columns (8 mm×30 cm, paired). The columns were previously equilibrated using 10 mM Tris-Cl buffer (pH 7.5) containing 60 mM NH$_4$Cl and 10 mM (CH$_3$COO)$_2$Mg. The reaction mixture (50 μl) was applied to the column and developed at a rate of 1.0 ml/min. Fractions were collected in 0.5 ml portions. To 0.5 ml of each fraction was added 3 ml of liquid scintillation cocktail Ready Safe (BECKMAN Instrument, Inc.) and the radioactivity of the mixture was measured by a liquid scintillation counter (BECKMAN Model LS5000TD). Protein markers for molecular weight determination on HPLC were purchased from Oriental Yeast Co., Ltd. The markers used were glutamic dehydrogenase (Mw 290,000), lactate dehydrogenase (Mw 142,000), enolase (Mw 67,000), adenylate kinase (Mw 32,000), and cytochrome C (Mw 12,400).

B. Results

Figure 3:
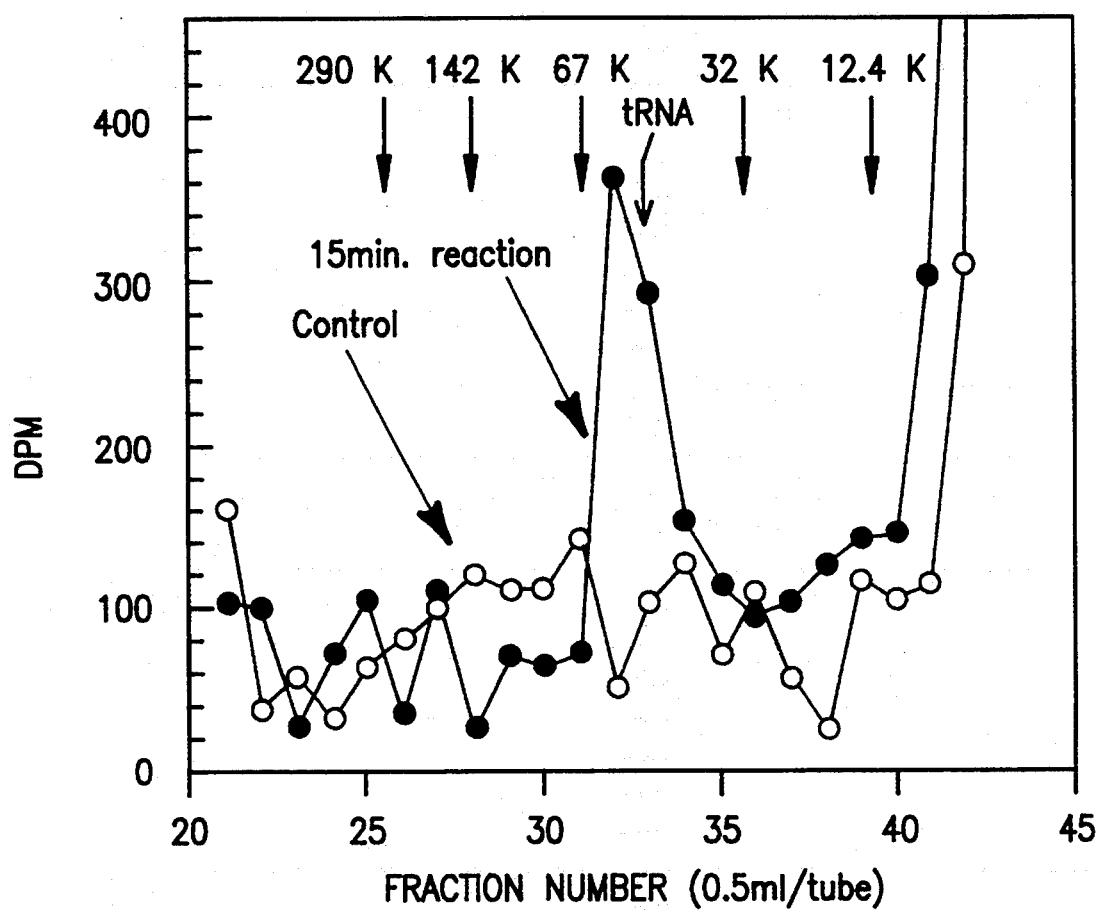
FIG. 3 is a graph depicting the result of fractionation of phenylalanyl-tRNA$^{Tyr}$ formed by the reverse reaction of aminoacyl-tRNA hydrolase by HPLC analysis.

To examine whether a misaminoacyl-tRNA can be synthesized by the reverse reaction of ARH, the hydrolytic activity of ARH was suppressed by adding an organic solvent and a large excess of an amine component (L-phenylalanine) to a reaction system, and a condensation reaction of the amino acid and tRNA was accelerated. L-phenylalanine and tyrosine-specific tRNA were reacted using the enzyme in the presence of 22% dimethyl formamide, and the amount of the labeled amino acid incorporated into a tRNA fraction was measured by high performance molecular sieve chromatography. As a result, it was found that no labeled amino acid was incorporated into the tRNA fraction in the absence of ARH, while a significant increase of a radioactive peak was observed in the tRNA fraction in the presence of ARH (FIG. 3).

The tRNA fraction which showed incorporation of phenylalanine was phenol extracted and ethanol precipitated to recover the tRNA. Most of the radioactivity was detected in the tRNA. The fraction containing the tRNA was then treated with ARH, again phenol extracted, and ethanol precipitated. In this case, the labeled amino acid was detected in the supernatant after the ethanol precipitation. These results indicate that in the presence of 22% dimethyl formamide and a large excess of L-phenylalanine, the hydrolytic activity of ARH was suppressed and a misaminoacyl-tRNA was synthesized from L-phenylalanine and tyrosine-specific tRNA by the reverse reaction (condensation) of ARH.

As described above, ARH used in the examples has a broad substrate specificity, and therefore, a variety of aminoacyl- and misaminoacyl-tRNAs can be synthesized utilizing the reverse reaction of the enzyme.

REFERENCES

1. T. G. Heckler, L. H. Chang, Y. Zama, T. Naka, M. S. Chorghade, and S. M. Hecht, Biochemistry, 23, 1468 (1984)
2. C. J. Noren, S. J. Anthony-Cahill, M. C. Griffith, and P. G. Schultz, Science, 244, 182 (1989)
3. M. E. Gallego and C. F. Heredia, Biochim. Biophys. Acta, 696, 57 (1982)
4. C. Fereiro and C. F. Heredia, Biochim. Biophys. Acta, 882, 410 (1986)
5. H. Takai, K. Sakato, N. Nakamizo, Y. Isowa, "Peptide Chemistry 1980", K. Okawa Ed., Protein Research Foundation, p. 213 (1981)
6. J. P. Jost and R. M. Bock, J. Biol. Chem., 244, 5866-5873 (1969)
7. N. De Groot, Y. Groner, and Y. Lapidot, Biochim. Biophys. Acta, 186, 286-296 (1969)
8. S. Nishimura, "Biochemistry Experimental Course", Japan Biochemical Society Ed., (Tokyo Kagaku Dojin), vol.7, P. 434 (1975)
9. A. Louie, E. Masuda, M. Yoder, and F. Jurnak, Anal. Biochem., 141, 402-408 (1984)
10. S. Nishimura, "Biochemistry Experimental Course", Japan Biochemical Society Ed., (Tokyo Kagaku Dojin), vol.7, P. 431 (1975)

What is claimed is:

1. A method for preparing L-tyrosyl-tRNA$^{Tyr}$ or L-phenylalanyl-tRNA$^{Tyr}$, wherein tRNA$^{Tyr}$ represents tyrosine-specific tRNA, comprising:

reacting tRNA$^{Tyr}$ with a large excess of L-tyrosine or L-phenylalanine in an aqueous solvent containing an organic solvent in the presence of an aminoacyl-tRNA hydrolase derived from *Fusarium culmorum* or *Artemia salina*, said large excess of L-tyrosine or L-phenylalanine being sufficient to suppress the hydrolytic activity of said aminoacyl-tRNA hydrolase so that said L-tyrosyl-tRNA$^{Tyr}$ or L-phenylalanyl-tRNA$^{Tyr}$ is synthesized; and separating the resultant L-tyrosyl-tRNA$^{Tyr}$ or L-phenylalanyl-tRNA$^{Tyr}$ from the reaction mixture by a chromatographic technique.

2. The method according to claim 1 wherein the organic solvent is dimethyl formamide and the aminoacyl-tRNA hydrolase is derived from *Fusarium culmorum*.

* * * * *